United States Patent [19]

Lutz

[11] Patent Number: 5,075,041
[45] Date of Patent: Dec. 24, 1991

[54] PROCESS FOR THE PREPARATION OF SECONDARY ALCOHOL SULFATE-CONTAINING SURFACTANT COMPOSITIONS

[75] Inventor: Eugene F. Lutz, Houston, Tex.
[73] Assignee: Shell Oil Company, Houston, Tex.
[21] Appl. No.: 545,025
[22] Filed: Jun. 28, 1990
[51] Int. Cl.$^5$ .......................... C11D 1/14; C11D 1/72; C11D 3/32; C11D 11/04
[52] U.S. Cl. .................................. 252/548; 252/550; 252/174.21; 252/545; 562/115; 558/39
[58] Field of Search .................. 252/550, 548, 174.21, 252/DIG. 1; 562/115; 558/39

[56] References Cited

U.S. PATENT DOCUMENTS

| | | | |
|---|---|---|---|
| 2,640,070 | 5/1953 | Dahmen | 260/460 |
| 2,945,818 | 7/1960 | Costine et al. | 252/353 |
| 3,676,523 | 7/1972 | Mason | 260/683.15 D |
| 3,686,351 | 8/1972 | Mason | 260/683.15 D |
| 3,737,475 | 6/1973 | Mason | 260/683.15 D |
| 3,825,615 | 7/1974 | Lutz | 260/683.15 D |
| 3,893,940 | 7/1975 | Ohogoshi et al. | 252/353 |
| 4,020,121 | 4/1977 | Kister et al. | 260/683.15 D |
| 4,052,342 | 10/1977 | Fernley et al. | 252/541 |
| 4,088,598 | 5/1978 | Williams | 252/135 |
| 4,175,092 | 11/1979 | Bakker et al. | 260/456 R |
| 4,226,797 | 10/1980 | Bakker et al. | 260/460 |
| 4,474,678 | 10/1984 | Lutz et al. | 252/174.21 |
| 4,544,493 | 10/1985 | Silvis | 252/89.1 |
| 4,857,213 | 8/1989 | Caswell | 252/8.75 |

FOREIGN PATENT DOCUMENTS 1194862 7/1970 European Pat. Off. .

OTHER PUBLICATIONS

F. Asinger, "Mono-Olefins: Chemistry and Technology", 1968, pp. 689-694.

*Primary Examiner*—Paul Lieberman
*Assistant Examiner*—Erin Higgins
*Attorney, Agent, or Firm*—Pamela J. McCollough

[57] ABSTRACT

This invention relates to a process for preparing secondary alkyl sulfate-containing surface active compositions substantially free of unreacted organic matter and water, which process comprises: a) sulfating a detergent range olefin having from about 8 to about 22 carbon atoms with concentrated sulfuric acid, b) neutralizing the product of step a) with a base dispersed in a nonionic surfactant having a boiling point higher than that of said detergent range olefin and its corresponding secondary alcohol, c) saponifying the product of step b), d) passing the product of step c) through a thin film evaporator to evaporate unreacted organic matter from said product and recovering said product.

33 Claims, No Drawings

PROCESS FOR THE PREPARATION OF SECONDARY ALCOHOL SULFATE-CONTAINING SURFACTANT COMPOSITIONS

Field of the Invention

This invention relates to a process for the preparation of secondary alcohol sulfate-containing surfactant compositions.

BACKGROUND OF THE INVENTION

This invention provides a process for preparing surfactant compositions comprising secondary alkyl sulfates which are substantially free of unreacted organic matter (UOM) and which are substantially free of water, thus making the compositions substantially free of inert diluents.

In conventional practice, secondary alkyl sulfates have been prepared by reaction of an olefin with sulfuric acid followed by neutralization of the intermediate secondary alkyl sulfuric acid with aqueous base, usually sodium hydroxide. The process is complicated by incomplete reaction of the starting olefin and by formation of dialkyl sulfates which saponify during the neutralization step, noted above, to equal molar amounts of secondary alkyl sulfate and secondary alcohol. These reactions, i.e., sulfation, neutralization and saponification, may be illustrated by the following equations:

$R^= + H_2SO_4 \rightarrow ROSO_3H + R_2SO_4$

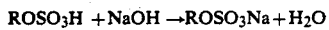

$ROSO_3H + NaOH \rightarrow ROSO_3Na + H_2O$

$R_2SO_4 + NaOH \rightarrow ROSO_3Na + ROH$

Unreacted olefin and secondary alcohol which can amount to 50% by weight or more of the starting olefin, are generally removed from the secondary alkyl sulfate by a process of extraction with an organic solvent as described in U.S. Pat. No. 4,175,092. The extraction process can be complicated by the formation of undesirable emulsions and gels as well as by the dissolution of some of the extracting solvent in the aqueous secondary alkyl sulfate phase. Extracting solvents frequently have objectionable odors and must be removed from the aqueous surfactant solution, an operation which can be accompanied by severe foaming difficulties. When extraction is complete the concentration of secondary alkyl sulfate in water is generally in the range of 20–40% by weight (F. Asinger, *Mono-Olefins: Chemistry and Technology*, 1968 pp. 689–694).

It would therefore be advantageous to have a process for preparing surfactant compositions utilizing secondary alkyl sulfates as the anionic component which eliminates the problems associated with solvent extraction for removal of the non-surface active organic material and which produces a product free of water, thus allowing maximum handling and blending flexibility.

An integrated process for preparing surfactant compositions has been found in which secondary alkyl sulfates derived from olefins can be generated in a manner such that the non-surface active material can be easily stripped from the secondary alkyl sulfates while at the same time producing a surfactant and/or detergent composition which is particularly useful for household laundry applications.

It is therefore an object of this invention to prepare surface active compositions containing olefin-drived secondary alkyl sulfates, which are substantially free of unreacted olefin and substantially free of water, in a nonionic surfactant having a boiling point higher than the olefin and its corresponding secondary alcohol. In the present invention, a surface active composition is prepared by reacting a detergent range olefin with concentrated sulfuric acid, removing excess sulfuric acid, neutralizing and saponifying the mixture in the presence of a base dispersed in a nonionic surfactant having a boiling point higher than the detergent range olefin and its corresponding secondary alcohol, and then passing the mixture through a falling film or wiped film evaporator to strip unreacted organic matter from the mixture, thereby producing a secondary alkyl sulfate-containing detergent composition which is anhydrous and substantially free of inert diluents.

SUMMARY OF THE INVENTION

This invention relates to a process for preparing secondary alkyl sulfate-containing surface active compositions substantially free of unreacted organic matter and water, which process comprises: (a) sulfating a detergent range olefin having from about 8 to about 22 carbon atoms with concentrated sulfuric acid, and, optionally, removing excess sulfuric acid by water wash, (b) neutralizing the product of step (a) with a base dispersed in a nonionic surfactant having a boiling point higher than said detergent range olefin and its corresponding secondary alcohol, (c) saponifying the product of step (b), (d) passing the product of step (c) through a thin film evaporator to evaporate unreacted organic matter from said product and recovering said product. The unreacted organic matter evaporated from the product can be recycled, if desired.

DESCRIPTION OF THE PREFERRED EMBODIMENTS

This invention relates to secondary alkyl sulfate-containing surface active compositions substantially free of unreacted organic matter and water prepared by a process which comprises sulfation of a detergent range olefin by adding concentrated sulfuric acid followed by water washing to remove excess sulfuric acid, neutralization with a base dispersed in a nonionic surfactant having a boiling point higher than that of said detergent range olefin and its corresponding secondary alcohol, saponification, and then distillation of unreacted organic matter, thus generating a surfactant composition comprising secondary alkyl sulfate and nonionic surfactant.

As used herein, the phrase "substantially free of unreacted organic matter and water" refers to detergent compositions which contain less than about 10 percent by weight, preferably less than about 5 percent by weight, of unreacted organic matter and less than about 5 percent by weight, preferably less than about 2 percent by weight, of water.

The detergent range olefins which are sulfated in step (a) of the instant invention are olefins containing from about 8 to about 22 carbon atoms. These olefins can be alpha olefins or internal olefins and they may be linear or branched, but are preferably linear or lightly branched. Single cut olefins or mixtures of olefins may also be used. In a particularly preferred embodiment, the olefin contains from about 12 to about 18 carbon atoms.

Preferred for use as olefin reactant for the practical reason of availability are the commercial olefin products in the $C_8$ to $C_{22}$ range. While commercial production of such olefins may be carried out by the cracking of paraffin wax, commercial production is more commonly accomplished by the oligomerization of ethylene using procedures well known in the art. The resulting oligomerization products are substantially of linear structure and thus products are substantially of linear structure. Commercial olefin products manufactured by ethylene oligomerization are marketed in the United States by Shell Chemical Company under the trademark Neodene and by Ethyl Corporation as Ethyl Alpha-Olefins. Specific procedures for preparing suitable linear olefins from ethylene are described in U.S. Pat. Nos. 3,676,523, 3,686,351, 3,737,475, 3,825,615 and 4,020,121. While most of such olefin products are comprised largely of alpha-olefins, higher linear internal olefins are also commercially produced, for example, by the chlorination-dehydrochlorination of paraffins, by paraffin dehydrogenation, and by isomerization of alpha-olefins. Linear internal olefin products in the $C_8$ to $C_{22}$ range are marketed by Shell Chemical Company and by Liquichemica Company. These commercial products, whether predominantly internal or alpha-olefins typically contain about 70 percent by weight or more, most often about 80 percent by weight or more, linear mono-olefins in a specified carbon number range (e.g., $C_{10}$ to $C_{12}$, $C_{11}$ to $C_{15}$, $C_{12}$ to $C_{13}$, $C_{15}$ to $C_{18}$, etc.), the remainder of the product being olefin of other carbon number or carbon structure, diolefins, paraffins, aromatics, and other impurities resulting from the synthesis process. Internal olefins marketed in the United States by Shell Chemical Company under the trademark Neodene are considered most preferred for use in the instant invention.

The concentrated sulfuric acid used to sulfate the detergent range olefins in step (a) is typically from about 75 percent by weight to about 96 percent by weight, preferably from about 85 percent by weight to about 96 percent by weight, in water. Generally, an amount of sulfuric acid in excess of the amount required to sulfate the olefins is used. Suitable amounts of sulfuric acid are generally in the range of from about 1 mole to about 15 moles of sulfuric acid per mole of olefin.

The sulfation reaction in step (a) is suitably carried out at temperatures in the range of from about $-20°$ C. to about $50°$ C., preferably from about $5°$ C. to about $40°$ C., and at pressures in the range of from about 1 atmosphere to about 5 atmospheres, preferably from about 1 atmosphere to about 2 atmospheres, and more preferably, about 1 atmosphere. Suitable residence times for the sulfation reaction range from a few minutes to several hours, preferably from about 2 minutes to about 10 hours and more preferably, from about 5 minutes to about 2 hours.

The sulfation reaction may be illustrated by the following equation:

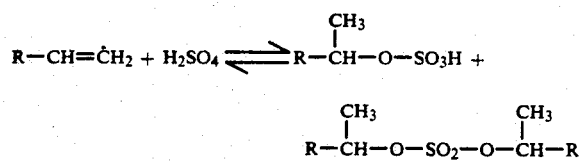

wherein R is an alkyl group having from about 6 to about 20 carbon atoms. The products of the sulfation reaction are primarily monoalkyl sulfuric acids and dialkyl sulfates along with unreacted olefin and unreacted sulfuric acid.

Following the sulfation of the olefins to monoalkyl sulfuric acids and dialkyl sulfates, the alkyl sulfuric acids may then be subjected to deacidification for the partial or substantially complete removal of the unconverted sulfuric acid. Suitable deacidification procedures include washing the sulfation reaction product with water at the same temperature at which the sulfation reaction in step (a) is carried out. While the present invention may be carried out with or without deacidification, in a preferred embodiment, the product of the sulfation reaction in step (a) is deacidified by the addition of small amounts of water thereto in order to remove as much unreacted sulfuric acid as possible.

Following the sulfation reaction in step (a), the monoalkyl and dialkyl sulfates thus produced are deacidified by water washing and then neutralized and saponified in the presence of a base dispersed in a nonionic surfactant having a boiling point higher than that of the detergent range olefin utilized in step (a) and its corresponding secondary alcohol, to form the corresponding sulfuric acid salts. Following the neutralization reaction in step (b). the dialkyl sulfates produced in the sulfation reaction are saponified or hydrolyzed in step (c) to form equal molar amounts of the desired monoalkyl sulfuric acid salts and secondary alcohol. Suitably, the neutralization and saponification reactions take place by the addition of one or more bases such as amines or ammonium or alkali metal or alkaline earth metal hydroxides, carbonates or bicarbonates dispersed in a nonionic surfactant having a boiling point higher than that of the detergent range olefin utilized, with sodium hydroxide being the preferred base. The amount of base added to the nonionic surfactant is based on the acidity of the monoalkylsulfuric acid phase after water washing and is suitably in the range of from about 1.1 meq/meq acid (milliequivalent per milliequivalent of acid) to about 2.5 meq/meq acid, preferably from about 1.3 meq/meq acid to about 1.9 meq/meq acid.

The nonionic surfactant utilized in the neutralization reaction in step (b) must have a higher boiling point than the boiling point of the detergent range olefin which is sulfated in step (a) and its corresponding secondary alcohol. The diluent must also be a liquid or at least be sufficiently flowable to pass through a thin film evaporator. Suitable nonionic surfactants include alkyl ethoxylates, alkylaryl ethoxylates and fatty acid diethanol amides.

Fatty acid diethanol amides suitable for use as nonionic surfactant in step (b) in the instant process are fatty acid amides derived from coconut fatty acids having from about 10 to about 14 carbon atoms.

In a preferred embodiment, the nonionic surfactant is an alcohol ethoxylate. The general class of alcohol ethoxylates useful in the neutralization reaction in step (b) as diluent is characterized by the chemical formula $R_1-O-(CH_2-CH_2O)_n-H$, wherein $R_1$ is a straight-chain or branched-chain alkyl group having in the range of from about 8 to about 18 carbon atoms, preferably from about 12 to about 18 carbon atoms, or an alkylaryl group having an alkyl moiety having from about 8 to about 12 carbon atoms, and n represents the average number of oxyethylene groups per molecule and is in the range of from about 1 to about 15, preferably from about 2 to about 12 and more preferably from about 2 to about 9. The alkyl group can have a carbon chain which is straight or branched, and the ethoxylate component can be a combination of straight-chain and branched molecules. Preferably, about 75 percent of the R groups in the instant composition are straight-chain. It is understood that R can be substituted with any substituent which is inert. Ethoxylates within this class are conventionally prepared by the sequential addition of ethylene oxide to the corresponding alcohol (ROH) in the presence of a catalyst.

The alcohol ethoxylate is preferably derived by ethoxylation of primary or secondary, straight-chain or branched alcohols. Suitably, the alcohols have from about 8 to about 18 carbon atoms, preferably from about 9 to about 15 carbon atoms, and more preferably from about 12 to about 15 carbon atoms. The most common ethoxylates in this class and the ones which are particularly useful in this invention are the primary alcohol ethoxylates, i.e., compounds of formula I in which R is an alkyl group and the $-O-(CH_2-CH_2O)_n-H$ ether substituent is bound to a primary carbon of the alkyl group.

Alcohols which are suitable to form alcohol ethoxylates for use in the present process include coconut fatty alcohols, tallow fatty alcohols, and the commercially available synthetic long-chain fatty alcohol blends, e.g., the $C_{12}$ to $C_{15}$ alcohol blends available as NEODOL 25 Alcohol (a registered trademark of product manufactured and sold by Shell Chemical Company), the $C_{12}$ to C14 alcohol blends available as Tergitol 24L (a registered trademark of product manufactured and sold by Union Carbide Corporation), and the $C_{12}$ to $C_{13}$ alcohol blends available, for example, as NEODOL 23 Alcohol (Shell).

Suitable alcohol ethoxylates can be prepared by adding to the alcohol or mixture of alcohols to be ethoxylated a calculated amount, e.g., from about 0.1 percent by weight to about 0.6 percent by weight, preferably from about 0.1 percent by weight to about 0.4 percent by weight, based on total alcohol, of a strong base, typically an alkali metal or alkaline earth metal hydroxide such as sodium hydroxide or potassium hydroxide, which serves as a catalyst for ethoxylation. The resulting mixture is dried, as by vapor phase removal of any water present, and an amount of ethylene oxide calculated to provide from about 1 mole to about 15 moles of ethylene oxide per mole of alcohol is then introduced and the resulting mixture is allowed to react until the ethylene oxide is consumed. A precalculated amount of ethylene oxide is added to achieve the desired level of ethoxylation. This amount can be readily determined by one of ordinary skill in the art with a minimal amount of experimentation. After the calculated amount of ethylene oxide has been added, the consumption of ethylene oxide can then be monitored by the decrease in reaction pressure.

The ethoxylation is typically conducted at elevated temperatures and pressures. Suitable reaction temperatures range from about 120° C. to about 220° C. with the range of from about 140° C. to about 160° C. being preferred. A suitable reaction pressure is achieved by introducing to the reaction vessel the required amount of ethylene oxide which has a high vapor pressure at the desired reaction temperature. For considerations of process safety, the partial pressure of the ethylene oxide reactant is preferably limited, for instance, to less than about 60 psia, and/or the reactant is preferably diluted with an inert gas such as nitrogen, for instance, to a vapor phase concentration of about 50 percent or less. The reaction can, however, be safely accomplished at greater ethylene oxide concentration, greater total pressure and greater partial pressure of ethylene oxide if suitable precautions, known to the art, are taken to manage the risks of explosion. A total pressure of between about 40 and 110 psig, with an ethylene oxide partial pressure between about 15 and 60 psig, is particularly preferred, while a total pressure of between about 50 and 90 psig, with an ethylene oxide partial pressure between about 20 and 50 psig, is considered more preferred. The pressure serves as a measure of the degree of the reaction and the reaction is considered to be substantially complete when the pressure no longer decreases with time.

It should be understood that the ethoxylation procedure serves to introduce a desired average number of ethylene oxide units per mole of alcohol ethoxylate. For example, treatment of an alcohol mixture with 3 moles of ethylene oxide per mole of alcohol serves to effect the ethoxylation of each alcohol molecule with an average of 3 ethylene oxide moieties per mole alcohol moiety, although a substantial proportion of alcohol moieties will become combined with more than 3 ethylene oxide moieties and an approximately equal proportion will have become combined with less than 3.

Specific nonionic surfactant compounds which can be used in the composition of the present invention include ethoxylated fatty alcohols, preferably linear primary or secondary monohydric alcohols with about $C_8$ to about $C_{18}$, preferably about $C_{12}$ to about $C_{15}$, alkyl groups and an average of about 1 to about 15, preferably about 2 to about 9, moles of ethylene oxide per mole of alcohol, and ethoxylated alkylphenols with $C_8$ to about $C_{12}$ alkyl groups, preferably about $C_8$ to about $C_{10}$ alkyl groups and an average of about 1 to about 12 moles of ethylene oxide per mole of alkylphenol.

A preferred class of nonionic ethoxylates is represented by the condensation product of a fatty alcohol having from about 12 to about 15 carbon atoms and from about 2 to about 12 moles of ethylene oxide per mole of fatty alcohol. Suitable species of this class of ethoxylates include: the condensation product of $C_{12}-C_{15}$ oxo-alcohols and 7 moles of ethylene oxide; the condensation product of narrow cut $C_{14}-C_{15}$ oxo-alcohols and 7 or 9 moles of ethylene oxide per mole of fatty (oxo)alcohol; the condensation of a narrow cut $C_{12}-C_{13}$ fatty (oxo)alcohol and 6.5 moles of ethylene oxide per mole of fatty alcohol. The fatty oxo-alcohols, while primarily linear, can have, depending upon the processing conditions and raw material olefins, a certain degree of branching. A degree of branching in the range from 15% to 50% by weight is frequently found in commercially available oxo-alcohols. Additionally, secondary alcohols may also be present.

The amount of nonionic surfactant in step (b) in the present invention is such that it is sufficient to disperse in the desired base and such that the amount of nonionic surfactant in the final surfactant composition is from about 15 percent by weight to about 65 percent by weight, preferably from about 20 percent by weight to about 60 percent by weight, and more preferably from about 30 percent by weight to about 45 percent by weight. Typically, the amount of nonionic surfactant utilized in step (b) is in the range of from about 20 percent by weight to about 60 percent by weight, and preferably from about 30 percent by weight to about 45 percent by weight, basis the weight of the final product.

The neutralization reaction in step (b) is suitably carried out at a temperature in the range of from about 20°

C. to about 65° C., and a pressure in the range of from about atmosphere to about 2 atmospheres. The neutralization time is typically in the range of from about 0.5 hours to about 1.0 hours.

The saponification reaction in step (c) is typically carried out at a temperature in the range of from about 100° C. to about 112° C. and a pressure of from about 1 atmosphere to about 2 atmospheres. The saponification reaction is generally carried out over a time period ranging from about 0.25 hours to about 2.0 hours.

The neutralization and saponification reactions may be illustrated by the following equations:

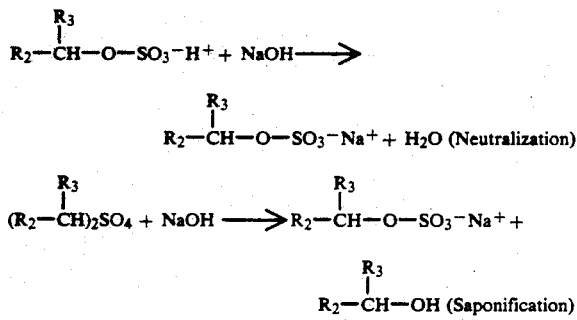

wherein $R_2$ and $R_3$ are alkyl groups having from about 1 to about 20 carbon atoms.

The product may be de-salted following the neutralization reaction. A de-salting treatment may be used in place of or in addition to the de-acidification described above depending on the extent of the de-acidification. Desalting is typically carried out by using an excess of base in the neutralization reaction which neutralizes the unreacted sulfuric acid to form the inorganic salts thereof in addition to neutralizing the secondary alkyl sulfuric acids. For example, sodium sulfate may be present when sodium hydroxide is the base in the neutralization. These inorganic salts may be removed as a separate phase by known methods such as, for example, filtration. However, removal of the inorganic salts in this manner results in a loss of sulfuric acid, since the organic salts thereof are normally discarded. For this reason, removal of unreacted sulfuric acid by deacidification via water washing following sulfation is preferred.

Following the neutralization and saponification reactions in steps (b) and (c), the product of step (c) is passed through a thin film evaporator in order to recover unreacted olefin and secondary alcohols. The thin film evaporator may suitably be a wiped film evaporator or a falling film evaporator. If desired, the secondary alcohol can be separated from unreacted olefin by means recognized by those skilled in the art such as, for example, distillation.

After the product is passed through an evaporator to remove unreacted organic matter, the resulting product is recovered. The product contains primarily secondary alkyl sulfate and nonionic surfactant, at least about 70 percent by weight to about 95 percent by weight, preferably about 85 percent by weight to about 95 percent by weight. The product generally contains from about 35 percent by weight to about 75 percent by weight, preferably from about 50 percent by weight to about 65 percent by weight secondary alkyl sulfate, and from about 20 percent by weight to about 60 percent by weight, preferably from about 30 percent by weight to about 45 percent by weight nonionic surfactant. Some residual level of sodium sulfate remains. The product typically contains less than about 12 percent by weight, preferably less than about 9 percent by weight, sodium sulfate.

The weight ratio of secondary alkyl sulfate to nonionic surfactant in the resulting surfactant composition can vary widely with weight ratios in the range of from about 0.5:4 to about 4:1, preferably from about 1:3 to about 3:1, and more preferably, from about 1:1 to about 2:1.

Typically, the compositions of the invention have a surface active material content after thin film evaporation, i.e. the percentage of secondary alkyl sulfate plus the percentage of nonionic surfactant, of at least about 70 percent by weight, preferably at least about 85 percent by weight, and more preferably, at least about 90 percent by weight of said composition. The compositions also contain from about 5 percent by weight to about 10 percent by weight sodium sulfate.

The surfactant compositions of the invention can be utilized in a variety of detergent applications. The surfactant compositions can be adsorbed at relatively low temperatures, about 85° C. or less, onto solid detergent materials such as, for example, sodium carbonate, in order to form dry detergent powders. The surfactant compositions can also be added to water or vice versa in order to form liquid detergents.

When an alcohol ethoxylate is used as the nonionic surfactant in the instant process, the surfactant compositions prepared may suitably be a detergent formulation of the general sort as is conventionally made of ethoxylate-containing surfactant compositions. Commonly, but not necessarily, such a formulation would contain the surfactant composition of the instant invention in a quantity between about one and about fifty percent by weight. The remainder of such formulation would be comprised of one or more additional components which are conveniently used in ethoxylate-containing formulations, such as, for example, water; detergent builders; sequestering agents; coloring agents; enzymes; perfumes; and other nonionic and anionic as well as cationic detergent active materials.

The ranges and limitations provided in the instant specification and claims are those which are believed to particularly point out and distinctly claim the present invention. It is, however, understood that other ranges and limitations which perform substantially the same function in substantially the same manner to obtain the same or substantially the same result are intended to be within the scope of the instant invention as defined by the instant specification and claims.

The invention will be described below by the following examples which are provided for purposes of illustration and are not to be construed as limiting the invention.

ILLUSTRATIVE EMBODIMENTS

Preparation of Surfactant Compositions
Sulfation

To a round-bottomed flask equipped with a paddle stirrer, thermometer, and addition funnel topped with a nitrogen blanket was added 64.21 grams of internal pentadecene and 64.22 grams of internal hexadecene. After cooling to 20°-21° C. 64.20 grams of 95% sulfuric acid was added at such a rate that the temperature was maintained at 20°-21° C. When acid addition was complete, 4.50 grams of distilled water was stirred for one hour and then phase separated. The upper phase contained 153.22 grams and the lower phase contained 34.54 grams.

Neutralization/Saponification

The upper phase from the sulfation above (153.22 grams) was added to a small stirred mixture of 32 grams of Neodol 23-6.5 alcohol ethoxylate (NEODOL is a trademark of Shell Chemical Company) and 29.31 grams of 50% sodium hydroxide, at 38°-39° C. over a period of forty-nine minutes. The pH was monitored and was 14 near the end of neutralization.

After neutralization, the mixture was heated with stirring to reflux (approximately 108° C.) and held at reflux for one hour.

A sample after thirty minutes at reflux gave an anionic concentration of 124.62 meq/100 grams. After one hour, the anionic concentration was 125.12 meq/100 grams. The alkalinity after one hour was 0.066 meq/gram or about 5.3% weight, basis anionic. Accordingly, 2.29 grams of 50% sodium hydroxide was added to increase the reserve alkalinity.

Thin Film Evaporation

To a wiped film evaporator at 145-146° C. and 119-130 mm Hg pressure, was added 200.89 grams of the neutralized/saponified product from the above step. The wiped film evaporator distillation required thirty-six minutes and produced 158.86 grams of bottoms product, 9.06 grams of organic and 27.29 grams of water in the distillate. The organic comprised 58 percent by weight $C_{15}$ internal olefin, 35.5 percent by weight $C_{16}$ internal olefin and 6.5 percent by weight $C_{15/16}$ alcohol. The bottom product contained an anionic concentration of 146.1 meq/100 grams.

147.11 Grams of the bottoms produced above in the first wiped film evaporator distillation was added to a wiped film evaporator at 145°-146° C. and 0.12-0.19 mm Hg pressure over a period of about twenty minutes. 103.71 Grams of product. 18.81 grams of organic tops and 1.5 grams of water were produced. The product contained an anionic concentration of 186.93 meq/100 grams.

The composition prepared in the above example contains about 63 percent by weight secondary alkyl sulfate, about 4.8 percent by weight sodium sulfate, and about 32.2 percent by weight alcohol ethoxylate.

What is claimed is:

1. A process for preparing secondary alkyl sulfate-containing surface active compositions substantially free of unreacted organic matter and water, which process comprises: (a) sulfating a detergent range olefin having from about 8 to about 22 carbon atoms with concentrated sulfuric acid. (b) neutralizing the product of step (a) with a base dispersed in a nonionic surfactant having a boiling point higher than that of said detergent range olefin and its corresponding secondary alcohol, (c) saponifying the product of step (b), (d) passing the product of step (c) through a thin film evaporator to evaporate unreacted organic matter from said product and recovering said product.

2. The process of claim 1 wherein said detergent range olefin has from about 12 to about 18 carbon atoms.

3. The process of claim 1 wherein said concentrated sulfuric acid is from about 75 percent by weight to about 96 percent by weight in water.

4. The process of claim 3 wherein said concentrated sulfuric acid is from about 85 percent by weight to about 96 percent by weight in water.

5. The process of claim 1 wherein said sulfation in step (a) is carried out at a temperature in the range of from about 5° C. to about 40° C. and a pressure in the range of from about atmosphere to about 2 atmospheres.

6. The process of claim 1 wherein following step (a), the product of step (a) is subjected to deacidification by water washing.

7. The process of claim 1 wherein said base in step (b) is selected from amines or ammonium, alkali metal or alkaline earth metal hydroxides, carbonates or bicarbonates.

8. The process of claim 7 wherein said base is sodium hydroxide.

9. The process of claim 1 wherein said nonionic surfactant in step (b) is an alcohol ethoxylate having a formula $R_1$—O—$(CH_2CH_2O)_n$—H, wherein $R_1$ is an alkyl group having from about 8 to about 18 carbon atoms or an arylalkyl group having an alkyl moiety having from about 8 to about 12 carbon atoms, and n represents the average number of oxyethylene groups per molecule and is a number in the range of from about 1 to about 12.

10. The process of claim 1 wherein said nonionic surfactant in step (b) is a fatty acid diethanol amide derived from a coconut fatty acid having from about 10 to about 14 carbon atoms.

11. The process of claim 1 wherein said neutralization in step (b) is carried out at temperatures in the range of from about 20° C. to about 65° C. and pressures in the range of from about 1 atmosphere to about 2 atmospheres.

12. The process of claim 1 wherein said saponification in step (c) is carried out at a temperature in the range of from about 100° C. to about 112° C. and a pressure of from about 1 atmosphere to about 2 atmospheres.

13. The process of claim 1 wherein in step (d), said thin film evaporator is a wiped film evaporator.

14. The process of claim 1 wherein said product recovered in step (d) contains from about 35 percent by weight to about 75 percent by weight secondary alkyl sulfate and from about 20 percent by weight to about 60 percent by weight nonionic surfactant.

15. The process of claim 14 wherein said product recovered in step (d) contains from about 50 percent by weight to about 65 percent by weight secondary alkyl sulfate and from about 30 percent by weight to about percent by weight nonionic surfactant.

16. The process of claim 9 wherein said product recovered in step (d) contains from about 35 percent by weight to about 75 percent by weight secondary alkyl sulfate and from about 20 percent by weight to about 60 percent by weight alcohol ethoxylate.

17. The process of claim 16 wherein said product recovered in step (d) contains from about 50 percent by weight to about 65 percent by weight secondary alkyl sulfate and from about 30 percent by weight to about 45 percent by weight alcohol ethoxylate.

18. The process of claim 10 wherein said product recovered in step (d) contains from about 35 percent by weight to about 75 percent by weight secondary alkyl sulfate and from about 20 percent by weight to about 60 percent by weight fatty acid diethanol amide.

19. The process of claim 18 wherein said product recovered in step (d) contains from about 50 percent by weight to about 65 percent by weight secondary alkyl sulfate and from about 30 percent by weight to about 45 percent by weight fatty acid diethanol amide.

20. A process for preparing secondary alcohol sulfate-containing surface active compositions substantially free of unreacted organic matter and water, which process comprises: (a) sulfating a detergent range olefin having from about 8 to about 22 carbon atoms with concentrated sulfuric acid, (b) neutralizing the product of step (a) with a base dispersed in an alcohol ethoxylate having a formula $R_1$—O—$(CH_2CH_2O)_n$—H, wherein $R_1$ is an alkyl group having from about 8 to about 18 carbon atoms or an arylalkyl group having an alkyl moiety having from about 8 to about 12 carbon atoms, and n represents the average number of oxyethylene groups per molecule and is a number in the range of from about to about 12, said alcohol ethoxylate having a boiling point higher than that of said detergent range olefin and its corresponding secondary alcohol, (c) saponifying the product of step (b). (d) passing the product of step (c) through a thin film evaporator to evaporate unreacted organic matter and recovering said product.

21. The process of claim 20 wherein said detergent range olefin has from about 12 to about 18 carbon atoms.

22. The process of claim 20 wherein said concentrated sulfuric acid is from about 75 percent by weight to about 96 percent by weight in water.

23. The process of claim 22 wherein said concentrated sulfuric acid is from about 85 percent by weight to about 96 percent by weight in water.

24. The process of claim 20 wherein said sulfation in step (a) is carried out at a temperature in the range of from about 5° C. to about 40° C. and a pressure in the range of from about 1 atmosphere to about 2 atmospheres.

25. The process of claim 20 wherein following step (a), the product of step (a) is subjected to deacidification by water washing.

26. The process of claim 20 wherein said base in step (b) is selected from amines or ammonium, alkali metal or alkaline earth metal hydroxides, carbonates or bicarbonates.

27. The process of claim 26 wherein said base is sodium hydroxide.

28. The process of claim 20 wherein said neutralization in step (b) is carried out at temperatures in the range of from about 20° C. to about 65° C. and pressures in the range of from about 1 atmosphere to about 2 atmospheres.

29. The process of claim 20 wherein said saponification in step (c) is carried out at a temperature in the range of from about 100° C. to about 112° C. and a pressure of from about 1 atmosphere to about 2 atmosphere.

30. The process of claim 20 wherein in step (d), said thin film evaporator is a wiped film evaporator.

31. The process of claim 20 wherein said product recovered in step (d) contains from about 35 percent by weight to about 75 percent by weight secondary alkyl sulfate and from about 20 percent by weight to about 60 percent by weight alcohol ethoxylate.

32. The process of claim 31 wherein said product recovered in step (d) contains from about 50 percent by weight to about 65 percent by weight secondary alkyl sulfate and from about 30 percent by weight to about 45 percent by weight alcohol ethoxylate.

33. The process of claim 20 wherein said composition contains at least about 85 percent by weight of secondary alkyl sulfate and alcohol ethoxylate.

* * * * *